US010925485B2

(12) United States Patent
Takeno et al.

(10) Patent No.: US 10,925,485 B2
(45) Date of Patent: Feb. 23, 2021

(54) DEFORMABLE MIRROR SYSTEM, CONTROL METHOD THEREFOR, AND OPHTHALMIC APPARATUS

(71) Applicant: CANON KABUSHIKI KAISHA, Tokyo (JP)

(72) Inventors: Kohei Takeno, Yokohama (JP); Kaishi Ohashi, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 382 days.

(21) Appl. No.: 14/842,996

(22) Filed: Sep. 2, 2015

(65) Prior Publication Data

US 2016/0089023 A1 Mar. 31, 2016

(30) Foreign Application Priority Data

Sep. 25, 2014 (JP) .............................. JP2014-194829

(51) Int. Cl.
| | | |
|---|---|---|
| *A61B 3/12* | (2006.01) | |
| *G02B 26/08* | (2006.01) | |
| *A61B 3/14* | (2006.01) | |
| *A61B 3/10* | (2006.01) | |
| *G02B 26/06* | (2006.01) | |

(52) U.S. Cl.
CPC .............. *A61B 3/12* (2013.01); *A61B 3/1015* (2013.01); *A61B 3/14* (2013.01); *G02B 26/06* (2013.01); *G02B 26/0825* (2013.01)

(58) Field of Classification Search
CPC ........... A61B 3/12; A61B 3/1015; A61B 3/14; G02B 26/06; G02B 26/0825

USPC ......................................................... 351/206
See application file for complete search history.

(56) References Cited

U.S. PATENT DOCUMENTS

2012/0287400 A1* 11/2012 Utagawa .................. A61B 3/14
351/206
2015/0131052 A1 5/2015 Saito et al.

FOREIGN PATENT DOCUMENTS

| JP | 2005-224328 A | 8/2005 |
| JP | 2007-025503 A | 2/2007 |

* cited by examiner

*Primary Examiner* — Thomas K Pham
*Assistant Examiner* — Mitchell T Oestreich
(74) *Attorney, Agent, or Firm* — Venable LLP

(57) ABSTRACT

For reducing a time utilized in an AO process, provided is a deformable mirror system, including: a deformable mirror capable of changing a shape of a reflecting surface by a deformation amount in accordance with an input signal; a light wavefront measurement apparatus configured to measure a light wavefront shape of reflected light from the deformable mirror; a conversion factor calculation apparatus configured to calculate a conversion factor used in obtaining the input signal from a variation in light wavefront shape of the reflected light with respect to a change in input signal; a shape difference calculation apparatus configured to calculate a shape difference between the light wavefront shape measured by the light wavefront measurement apparatus and a light wavefront shape calculated from the input signal; and a conversion factor update unit configured to update the conversion factor in accordance with the calculated shape difference.

12 Claims, 9 Drawing Sheets

DEFORMABLE MIRROR SYSTEM, CONTROL METHOD THEREFOR, AND OPHTHALMIC APPARATUS

BACKGROUND OF THE INVENTION

Field of the Invention

The present invention relates to a deformable mirror system forming an adaptive optics system used in an astronomical telescope, a fundus observation apparatus, or the like, and to an ophthalmic apparatus using the deformable mirror system.

Description of the Related Art

Currently, as ophthalmic equipment, various kinds of optical equipment are used. Among others, as optical equipment for observing an eye, various kinds of equipment such as an anterior ocular segment imaging apparatus, a fundus camera, a confocal scanning laser opthalmoscope (SLO), and an optical coherence tomography (OCT) apparatus are used.

An eyeball as an object to be observed is formed of a cornea, aqueous humor, a lens, a vitreous body, and a retina, and may be viewed as four lenses cemented together. However, for the reason that refractive indices of the cornea and the lens are not uniform and other such reasons, measuring light or the like that has passed through the eyeball has aberration, and the aberration may hinder the observation of the eyeball. In order to eliminate an influence of the aberration, adaptive optics technology (AO technology) has been utilized in ophthalmic optical equipment. The AO technology is a technology of measuring and correcting the aberration in real time. More specifically, aberration of a light wavefront that has passed through an eye to be inspected is measured by a wavefront sensor such as a Shack-Hartmann sensor. Then, a deformable mirror is arranged on an optical path along which the light passes, and a shape of a reflecting surface of the deformable mirror is changed to cancel the aberration of the wavefront, and hence to correct the aberration of the light wavefront resulting from the aberration of the eye.

An example of utilizing the above-mentioned AO technology in fundus observation is the invention disclosed in Japanese Patent Application Laid-Open No. 2007-25503. This document has a feature that, in fabricating an AO unit using a deformable mirror, individual differences occur in surface shape and deformation property due to manufacturing, assembling, and a stress of a mirror material, and hence calibration is performed to fabricate an ideal voltage template.

In an ophthalmic apparatus such as a fundus observation apparatus using recent AO technologies, it is required to perform correction of various diopters such as myopia and hyperopia of a patient by the deformable mirror, but there are many problems for the realization. Among others, in a case where a high diopter is to be corrected, nonlinearity of the deformable mirror may become problematic. For example, in order to subject severe myopia as strong as −10 diopter to the diopter correction by using the deformable mirror, a large deformation of about 50 μm in P-V value is required. Therefore, in a case of reducing the time to capture an image in consideration of a burden on the patient, it is required to efficiently correct the nonlinearity accompanying the large deformation.

However, in the related-art example described in Japanese Patent Application Laid-Open No. 2007-25503 above, a large number of calculations are required to update the voltage template as the need arises, and it takes long time to obtain a desired shape of the deformable mirror.

SUMMARY OF THE INVENTION

The present invention has been made in view of the above-mentioned circumstances, and therefore has an object to reduce the time it takes for reflected light from a deformable mirror system utilized in an AO unit to reach a desired light wavefront shape.

In order to solve the above-mentioned problems, according to one embodiment of the present invention, there is provided a deformable mirror system, including: a deformable mirror capable of changing a shape of a reflecting surface by a deformation amount in accordance with an input signal; a light wavefront measurement apparatus configured to measure a light wavefront shape of reflected light from the deformable mirror; a conversion factor calculation apparatus configured to calculate a conversion factor used in obtaining the input signal from a variation in light wavefront shape of the reflected light with respect to a change in input signal; a shape difference calculation apparatus configured to calculate a shape difference between the light wavefront shape measured by the light wavefront measurement apparatus and a light wavefront shape calculated from the input signal; and a conversion factor update unit configured to update the conversion factor in accordance with the calculated shape difference.

According to the present invention, the deformable mirror system utilized in the AO unit may reduce the time it takes to reach the desired light wavefront shape, and hence reduce measurement time with an ophthalmic apparatus or the like.

Further features of the present invention will become apparent from the following description of exemplary embodiments with reference to the attached drawings.

DESCRIPTION OF THE EMBODIMENTS

Now, exemplary embodiments of the present invention are described with reference to the drawings. Note that, the following embodiments are not intended to limit the present invention defined in the scope of claims, and not all combinations of features described in the embodiments are essential to solving means of the present invention.

First Embodiment

<Fundus Imaging Apparatus>
A configuration of a fundus imaging apparatus to which a deformable mirror system according to the present invention is applied is described with reference to FIG. 1. Note that, in this embodiment, an object to be inspected, which is a measurement target, is an eye, and aberration of light wavefront generated by the eye to be inspected is corrected by an AO unit to capture an image of a fundus.

Figure 1:
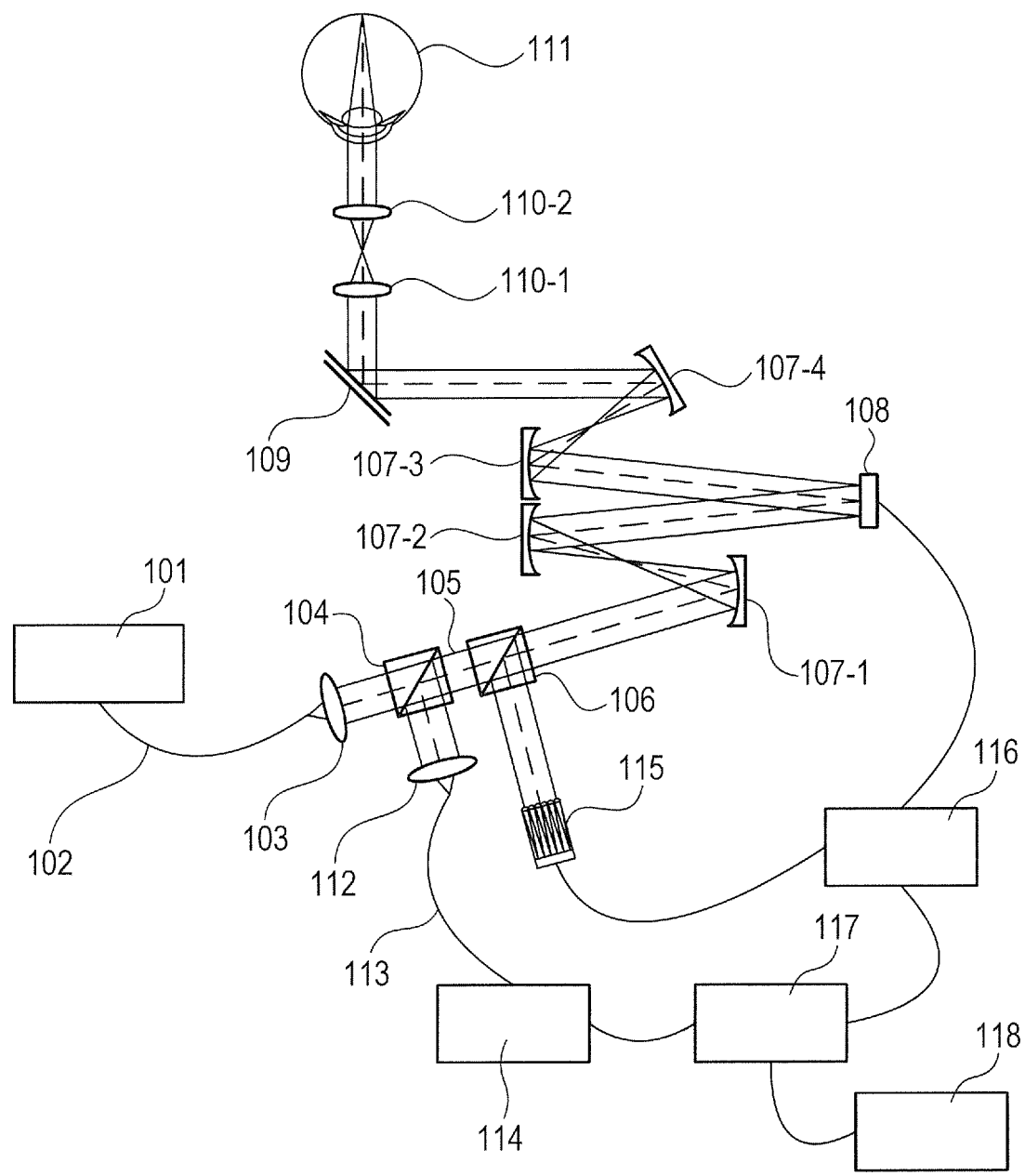
FIG. 1 is a schematic diagram for illustrating structure of a fundus imaging apparatus according to a first embodiment of the present invention.

Moreover, in FIG. 1, the deformable mirror system according to the present invention includes a deformable mirror 108, a wavefront sensor 115, and an AO control unit 116. The deformable mirror 108 changes a shape of a reflecting surface by a deformation amount in accordance with an input signal, which is to be described later. The wavefront sensor 115 functions as a light wavefront measurement unit configured to measure a light wavefront shape of reflected light from the deformable mirror 108. The AO control unit 116 functions as a conversion factor calculation unit configured to calculate a conversion factor, which is to be described later, a storage unit configured to store the conversion factor, and a drive control device configured to drive the deformable mirror.

In the fundus imaging apparatus, as a light source 101, a super luminescent diode (SLD) light source configured to emit light having a wavelength of 840 nm is used. The wavelength of the light from the light source 101 is not particularly limited, but in order to reduce brightness for a subject and maintain a resolution in capturing the image of the fundus, it is preferred to use light in a wavelength range of about 800 to 1,500 nm. Note that, the SLD light source is used in this embodiment, but a laser or the like may also be used as the light source. Moreover, the light source is shared in obtaining measuring light for capturing the image of the fundus and for measuring the wavefront in this embodiment, but a configuration in which the measuring light for each case is obtained from different light sources and the measuring light is multiplexed along the way of an optical path may be employed.

The light irradiated from the light source 101 passes through a single-mode optical fiber 102 and is irradiated as collimated light (measuring light 105) by a collimator 103. The irradiated measuring light 105 is transmitted through a light splitting unit 104 formed of a beam splitter and is guided to the AO unit.

The AO unit includes a second light splitting unit 106, the wavefront sensor 115, the deformable mirror 108, and reflecting mirrors 107-1 to 107-4 configured to guide light to the components.

Figure 2A:
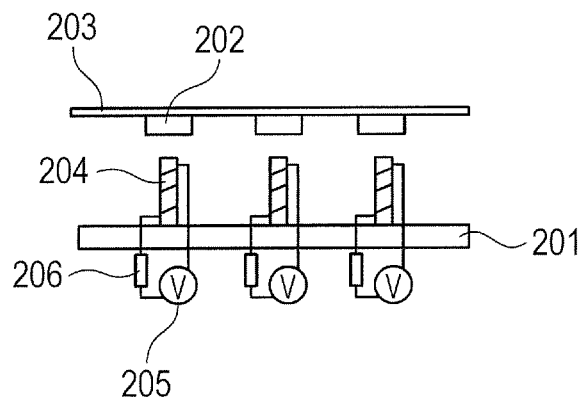
FIGS. 2A, 2B and 2C are schematic diagrams each for illustrating a structure example of a deformable mirror.

Note that, in this embodiment, a deformable mirror of electromagnetic type is used as the deformable mirror 108. In FIG. 2A, a schematic diagram of structure of the deformable mirror of electromagnetic type is illustrated. In the deformable mirror, a plurality of coils 204 are arranged on a substrate 201, and a voltage 205 applied to the coils 204 is controlled to control an electromagnetic force to be generated. Note that, in the exemplified deformable mirror, resistors 206 are inserted in series with the coils 204. In addition, magnets 202 are mounted on a membrane 203 at positions opposed to the coils 204 to form a mechanism in which the membrane 203 is deformed in accordance with a magnitude of the electromagnetic force generated by the coils 204.

Figure 2B:
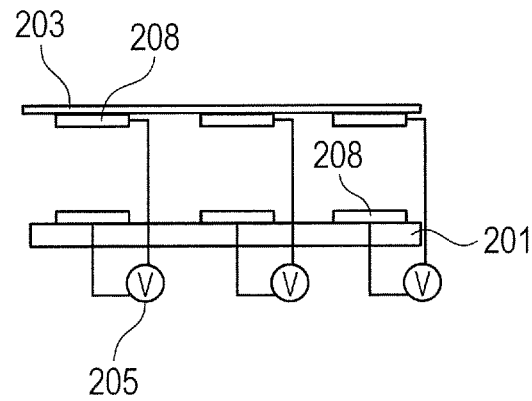
Figure 2C:
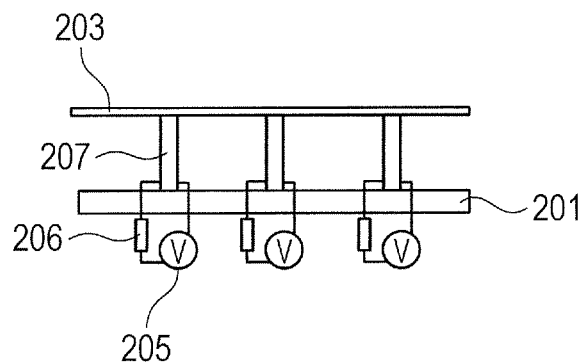

Note that, in this embodiment, the deformable mirror of electromagnetic type is used, but a deformable mirror of electrostatic type illustrated in FIG. 2B or of piezoelectric type illustrated in FIG. 2C may be used. In the deformable mirror of electrostatic type, a force generated by applying the voltage 205 to electrodes 208 is utilized to deform the membrane 203. Meanwhile, in the deformable mirror of piezoelectric type, the voltage 205 is applied to a piezoelectric material 207 such as PZT to deform the membrane 203. Also in those deformable mirrors, the resistors 206 are inserted in series in the circuit as in the deformable mirror of electromagnetic type illustrated in FIG. 2A.

The reflecting mirrors 107-1 to 107-4 are placed so that at least a pupil of an eye 111, the wavefront sensor 115, and the deformable mirror 108 are optically conjugate. Moreover, as the light splitting unit 106, a beam splitter is used in this embodiment.

The measuring light 105 that has been transmitted through the light splitting unit 106 is reflected by the reflecting mirrors 107-1 and 107-2 to enter the deformable mirror 108. The measuring light 105 reflected by the deformable mirror 108 is emitted to the reflecting mirror 107-3.

In FIG. 1, light reflected by the reflecting mirrors 107-3 and 107-4 is scanned in one dimension or two dimensions by a scanning optical system 109. In this embodiment, two Galvano scanners are used for main scanning (fundus horizontal direction) and for sub scanning (fundus vertical direction) in the scanning optical system 109. Note that, in a case where the image is to be captured at higher speed by the scanning optical system 109, a resonance scanner may be used for the main scanning in the scanning optical system 109. Moreover, in order to arrange the scanners in the scanning optical system 109 at optically conjugate positions, an apparatus configuration in which an optical element such as a mirror or a lens is used between the scanners may be employed.

The measuring light 105 scanned by the scanning optical system 109 is irradiated on the eye 111 through eyepiece lenses 110-1 and 110-2. The measuring light irradiated on the eye 111 is reflected or scattered by the fundus. Adjustment of positions of the eyepiece lenses 110-1 and 110-2 allows irradiation of the measuring light 105 optimal for a diopter of the eye 111. The lenses are used in an eyepiece unit here, but the eyepiece unit may include a spherical mirror or the like.

Reflected light reflected or scattered on a retina of the eye 111 travels along the path that the light traveled at the time of entering in an opposite direction, and a part of the reflected light is reflected by the light splitting unit 106 to enter the wavefront sensor 115.

Figure 3A:
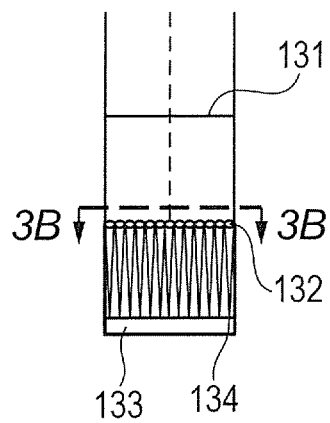
FIGS. 3A and 3B are schematic views for illustrating structure of a Shack-Hartmann sensor.
Figure 3B:
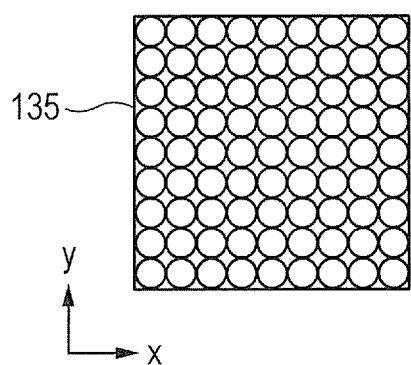

In this embodiment, a Shack-Hartmann sensor is used as the wavefront sensor 115. FIG. 3A and FIG. 3B are schematic views of structure of the Shack-Hartmann sensor. In the Shack-Hartmann sensor, a light beam 131 of which a wavefront is to be measured is condensed on a focal plane 134 of a charge coupled device (CCD) sensor 133 through a microlens array 132. FIG. 3B is a view from a position indicated by the cross section 3B-3B in FIG. 3A, and the microlens array 132 includes a plurality of microlenses 135. The light beam 131 is condensed on the CCD sensor 133 through the microlenses 135, and hence the light beam 131 is condensed after being split into the number of spots corresponding to the number of microlenses 135.

Note that, in this embodiment, the Shack-Hartmann sensor is used as the wavefront sensor, but the wavefront sensor for use is not limited thereto. For example, another wavefront measurement unit such as a curvature sensor, or a method in which the wavefront is determined by inverse calculation based on formed point images may be used.

In FIG. 1, the reflected light from the retina, which has been transmitted through the light splitting unit 106, is partly reflected by the light splitting unit 104. The reflected partial light is guided to a light intensity sensor 114 through a collimator 112 and an optical fiber 113. The guided partial light is converted into electric signals by the light intensity sensor 114, and constructed into an image as a fundus image by a control unit 117. The constructed fundus image is displayed on a display 118. Moreover, based on the obtained image, the control unit 117 determines a defocus amount with respect to the retina of the eye 111. Note that, as a method of detecting the defocus amount, a known method is used, and hence a detailed description thereof is omitted here. The detection of the defocus amount is executed by a defocus amount detection unit formed of the control unit 117 described above or the like to detect the defocus amount with respect to the object to be inspected on which the reflected light has been reflected.

The wavefront sensor 115 is connected to the AO control unit 116 to transmit the wavefront of the received light to the AO control unit 116. The deformable mirror 108 is connected to the AO control unit 116 to perform modulation instructed from the AO control unit 116, that is, deformation of the reflecting surface. Based on the light wavefront shape measured by the wavefront sensor 115, the AO control unit 116 calculates such a deformation amount (correction amount) as to correct the light wavefront into a wavefront without the aberration, and instructs a wavefront correction device 108 to perform such modulation. The measurement of the wavefront and the instruction to the wavefront correction device are repeatedly executed to perform feedback control so that an optimal wavefront is always obtained. In this embodiment, the light wavefront shape is approximated by superposition of Zernike polynomials to determine coefficients of each term.

Here, in order to drive the deformable mirror 108, the conversion factor is calculated in the AO control unit 116. The conversion factor is a correction value for a signal used in calculating the input signal to the deformable mirror required to change the light wavefront shape by a reference amount. Here, the AO control unit 116 functions as a conversion factor calculation unit configured to calculate the conversion factor used in obtaining a new input signal from an amount of change in wavefront shape of the reflected light with respect to a change in input signal.

The conversion factor is determined based on an influence function $f_{nm}$, which is the amount of change in light wavefront shape per unit input signal to the deformable mirror. For example, in a case where a voltage of $v_n$ volts is applied to the n-th actuator of the deformable mirror, if a coefficient of the term m of the Zernike polynomials measured by the wavefront sensor 115 is changed by $z_m$ micrometers, the influence function $f_{nm}$ is expressed as follows:

$$f_{nm} = z_m/v_n \, \mu m/V \qquad \text{Expression 1,}$$

where n is the number of actuators, and takes a value in a range of n=1 to 97. Moreover, m takes a value in a range determined by the order of the Zernike polynomials, and m=3 to 36 for a seventh-order Zernike polynomial. Here, m=0 indicates piston, and m=1 and 2 indicates tilt, which are excluded from calculation of the influence function. The influence function $f_{nm}$ is a set of 97×34 values.

The influence function $f_{nm}$ may be obtained for all the actuators, a two-dimensional matrix F having $f_{nm}$ as a value at the n-th row and the m-th column may be generated, and a pseudoinverse matrix of F may be calculated to determine a conversion factor $a_{mn}$.

Moreover, when a one-dimensional vector having $v_n$ as the n-th value is represented by V, and a one-dimensional vector having $z_m$ as the m-th value is represented by Z, the vectors V and Z and the matrix F have the following relationship:

$$Z = FV \qquad \text{Expression 2.}$$

In order to solve Expression 2 in terms of the vector V, a matrix that acts on the two-dimensional matrix F from the left to generate an identity matrix I may be multiplied. Such matrix is called an inverse matrix. However, for the two-dimensional matrix F in this embodiment, when the number of rows is represented by N, and the number of columns is represented by M, N>M, and there is no inverse matrix premised on a square matrix (M=N). Therefore, a pseudoinverse matrix $F^+$, which is a generalized inverse matrix that acts on a two-dimensional matrix A, which is a non-square matrix, from the left to generate the identity matrix, is calculated. For the calculation of the pseudoinverse matrix, singular value decomposition is used. The pseudoinverse matrix $F^+$ acts on Expression 2 from the left, and the pseudoinverse matrix's property $F^+F = I$ is used to determine V as follows.

$$V = F^+ Z \qquad \text{Expression 3.}$$

Here, Expression 3 expresses an input signal required to obtain a desired Zernike coefficient, and the element at the m-th row and the n-th column of $F^+$ is the conversion factor $a_{mn}$.

Next, a flow of capturing an image of the fundus by using the AO while applying the present invention is described with reference to FIG. 4, FIG. 5, and FIG. 7.

Figure 4:
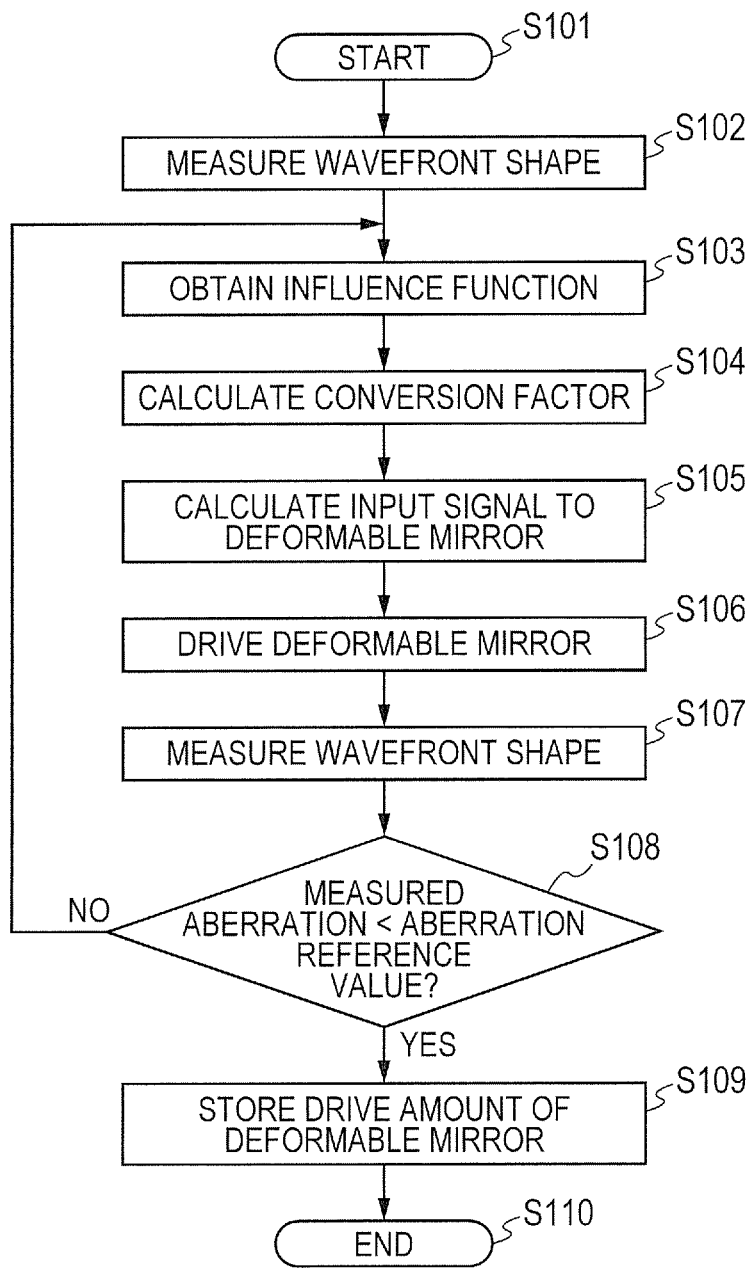
FIG. 4 is a flow chart of an initialization process in the first embodiment of the present invention.

FIG. 4 is a flow for illustrating an initialization process in which an initial value of the conversion factor is determined to eliminate an influence of initial strain of the deformable mirror. In the initialization process, a model eye is used as the eye 111 in FIG. 1. First, in Step S101, the initialization process is started. In the initialization process, a drive amount in a case where light is reflected by the deformable mirror 108 and the reflected light has a planar wavefront is determined. In Step S102, the light wavefront shape of reflected light from the model eye 111 or the like that has passed through the deformable mirror 108 is measured by the wavefront sensor 115, and the coefficients of the Zernike polynomials are determined based on a result of the measurement in the AO control unit 116. Next, in Step S103, similarly in the AO control unit 116, Expression 1 described above is used to determine the influence function, and further in Step S104, Expression 3 is used to determine the conversion factor. Next, based on the obtained conversion factor, in Step S105, the input signal to the deformable mirror 108 required to make the wavefront of the light to reach the wavefront sensor 115 planar is calculated, and in Step S106, the signal is input to the deformable mirror 108 to drive the same.

In Step S107, the light wavefront shape of the reflected light or the like that has passed through the deformable mirror 108 after the deformation is measured again. In Step S108, a measured aberration of the light wavefront resulting from the initial strain of the deformable mirror 108 and a predetermined aberration reference value are compared. In a case where the measured aberration is larger than the aberration reference value, it is determined that the initialization is not performed even after the driving, and the flow returns to Step S103 to repeat the steps up to Step S107 again. In a case where it is determined in Step S108 that the measured aberration is smaller than the aberration reference value, it is determined that initialization is finished, and the flow proceeds to Step S109. In order to make the reflecting surface of the deformable mirror flat when the image of the fundus is captured, the drive amount of the deformable mirror is stored in Step S109, and the initialization process is ended in Step S110.

Figure 5:
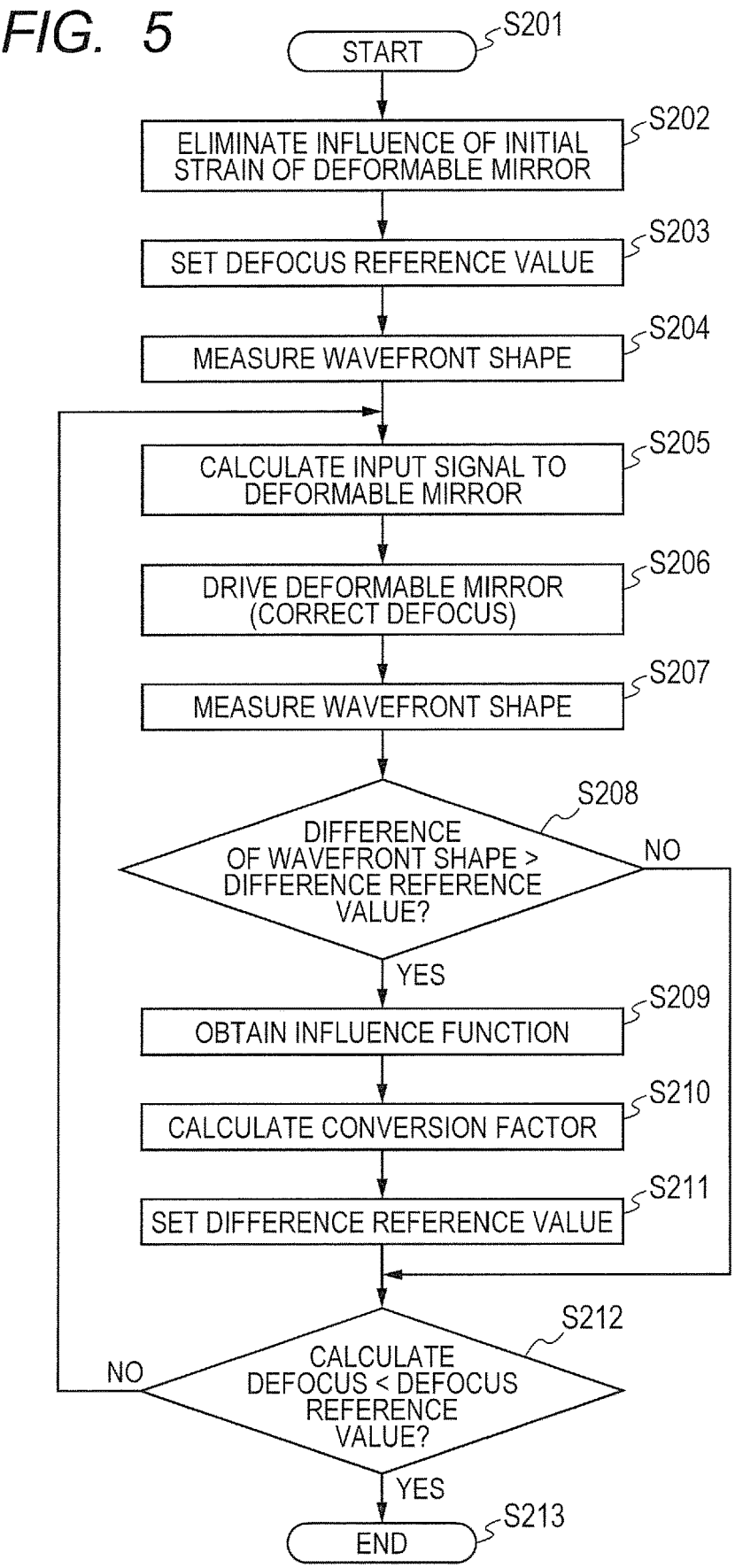
FIG. 5 is a flow chart of a diopter correction process in the first embodiment of the present invention.

Next, referring to the flow of FIG. 5, correction of the diopter of the eye 111 of the subject is actually performed. In Step S201, the diopter correction is started. In Step S202, based on the drive amount of the deformable mirror 108 stored in Step S109 in the initialization process described above, the influence of the initial strain of the deformable mirror 108 is eliminated. Next, in Step S203, a defocus reference value for use in determination in Step S208 and Step S212 is set. With respect to an rms value of 0.03 μm, which is the measured aberration at which an influence on an image obtained by capturing a fundus image is regarded as being sufficiently small, in consideration of the fact that the measured aberration other than the defocus is also included, the defocus reference value may be set to 0.01 μm, for example. Alternatively, the defocus reference value may be set larger than 0.01 μm in a case where fixation of the eye to be inspected 111 is unstable, or may be set smaller than 0.01 μm in a case where the measured aberration other than the defocus is large. Those values may be input sequentially, or may be selected from a table stored in a memory or the like associated with the control unit 117. Alternatively, those values may be contained in ID information or the like of the subject to be used as appropriate. In Step S204, a light wavefront shape of the reflected light or the like that has passed through the eye to be inspected 111 is measured to determine the measured aberration generated by the eye to be inspected Ill. In Step S205, the conversion factor or the like obtained in the initialization process is used again to calculate the input signal to the deformable mirror 108 required to correct the measured aberration.

In Step S206, the deformable mirror 108 is driven so as to correct the defocus obtained by the control unit 117, and in Step S207, the light wavefront shape of the reflected light after the driving is measured. After the measurement, in Step S208, a difference of the light wavefront shape and a shape difference reference value are compared. The term "difference of the light wavefront shape" as used herein refers to an absolute magnitude of a difference between the deformation amount of the light wavefront shape, which is calculated based on the conversion factor $a_{mn}$ and the input signal to the deformable mirror 108, and an actual variation in light wavefront shape, which is obtained by a comparison between the original light wavefront shape and the light wavefront shape actually measured in Step S207. The calculation of the shape difference is executed by a module region in the control unit 117 functioning as a shape difference calculation unit configured to calculate the shape difference between the light wavefront shape measured by the light wavefront measurement unit and the light wavefront shape based on the input signal.

In a case where the difference of the light wavefront shape exceeds the shape difference reference value, it is determined that nonlinearity occurs in the deformable mirror. Therefore, the influence function is obtained again in Step S209, and the conversion factor is also calculated in Step S210. In other words, the conversion factor is updated based on the calculated shape difference, and more specifically, on a result of the comparison between the shape difference and the shape difference reference value by a module region in the control unit 117 functioning as a conversion factor update unit. In Step S211, the shape difference reference value for use in the determination in Step S208 is set again in accordance with the nonlinearity of the deformable mirror, and more specifically, with the update of the conversion factor. The shape difference reference value is used as a threshold value of the shape difference, and the update of the threshold value is executed by a module region in the control unit 117 functioning as a threshold value update unit. In a case of reducing frequencies of occurrence of the obtainment of the influence function and the calculation of the conversion factor, it is preferred to increase the shape difference reference value.

In a case where it is determined in Step S208 that the difference of the light wavefront shape does not exceed the shape difference reference value, it is determined that the aberration is sufficiently corrected, and the flow proceeds to Step S212. In Step S212, the focus is calculated again in this state to compare a value of the calculated defocus and the defocus reference value. At this time, in a case where the defocus falls below the defocus reference value, the flow proceeds to Step S213, and a diopter correction process is ended. In a case where it is determined in Step S212 that the defocus does not fall below the defocus reference value, the flow returns to Step S205, where the input signal to the deformable mirror 108 is calculated again. The above-mentioned steps are performed to obtain a fundus image in which the influence of the diopter of the eye to be inspected is sufficiently suppressed. In other words, depending on the result of the comparison between the detected defocus amount and the defocus reference value, the image of the fundus of the eye to be inspected based on the reflected light is permitted to be captured. The permission of the image capturing is given by an image capturing permission unit provided in the control unit 117.

An effect obtained by performing the diopter correction illustrated in the flow of FIG. 5 is described with reference to FIG. 6A to FIG. 6C.

Figure 6A:
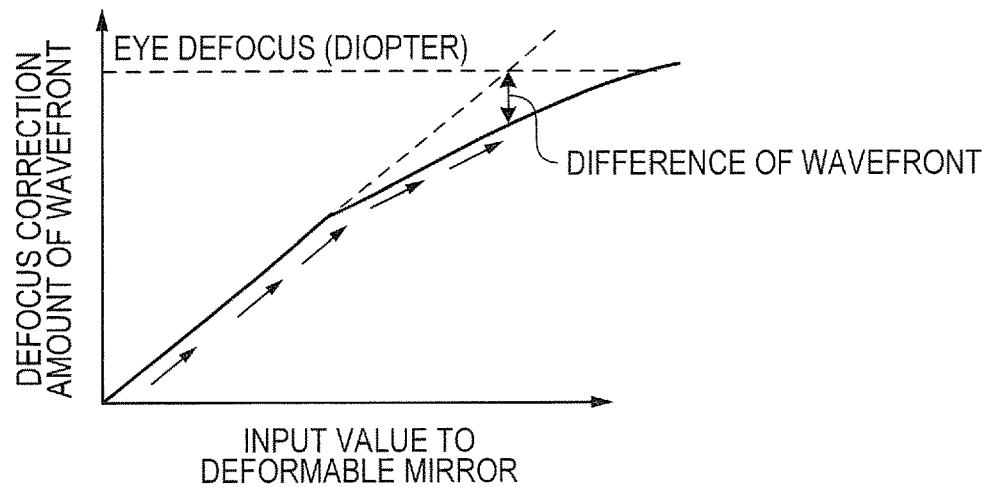
FIGS. 6A, 6B and 6C are graphs each for showing a relationship of a defocus correction amount of a light wavefront with respect to an input value to the deformable mirror.
Figure 6B:
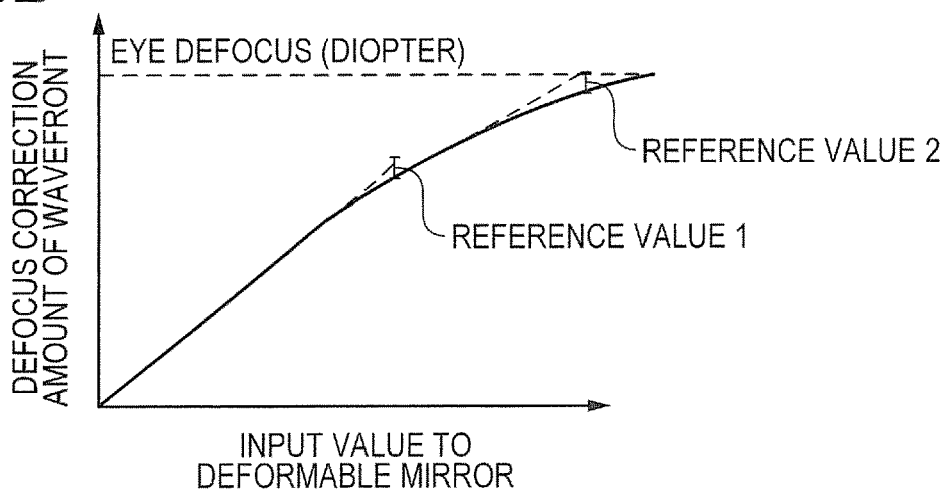
Figure 6C:
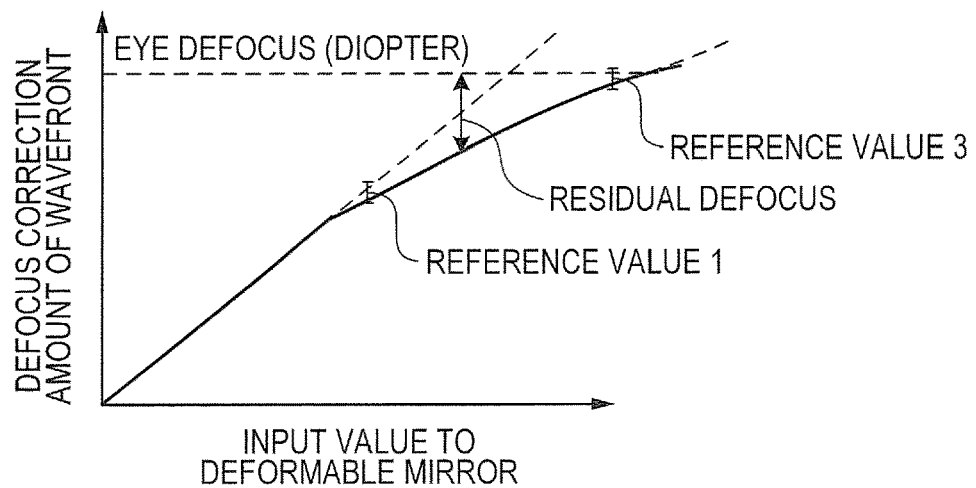

FIG. 6A to FIG. 6C are graphs each for showing a situation in which the defocus is corrected by the deformation of the deformable mirror, in which the horizontal axis indicates an input value to the deformable mirror, and the vertical axis indicates an amount by which the defocus is corrected with the deformation of the deformable mirror. The relationship between the input value and the correction amount is indicated by the curve. Note that, in the figures, a bend of the curve due to the nonlinearity is exaggerated. Moreover, an eye defocus amount is indicated by the dotted line on the same graphs. FIG. 6A is a graph for showing a situation in which the initial value of the conversion factor is used to correct the defocus. As the deformation of the deformable mirror becomes larger, a defocus correction amount of the light wavefront obtained with respect to the input value to the deformable mirror becomes smaller, and hence the difference of the light wavefront shape described above is generated.

FIG. 6B is a graph for showing a case of updating the conversion factor in the case where the difference of the light wavefront exceeds the reference value. When the input value to the deformable mirror becomes large, and when the difference of the light wavefront shape becomes larger than a defocus reference value 1, the obtainment of the influence function and the calculation of the conversion factor are performed. With the use of the obtained conversion factor, the correction amount in accordance with a unit increment of the input value becomes smaller, and the slope of the curve in the figure becomes gentler. Moreover, along with the use of the conversion factor, a new defocus reference value 2 is set. At this stage, the defocus amount has not reached the eye defocus, and hence the input value to the deformable mirror is further increased to increase the correction amount. Thereafter, when the difference of the light wavefront shape becomes larger than the defocus reference value 2, the obtainment of the influence function and the calculation of the conversion factor are performed again to update the conversion factor and set a new defocus reference value.

In other words, the residual defocus amount is calculated based on the detected defocus amount and the defocus amount calculated from the input signal. Moreover, in response to a comparison between the calculated residual defocus amount and a residual defocus reference value, the residual defocus reference value is updated. In this embodiment, the control unit 117 includes a residual defocus amount calculation unit configured to calculate the residual defocus amount, and a residual defocus reference value update unit configured to update the defocus reference value.

Figure 7:
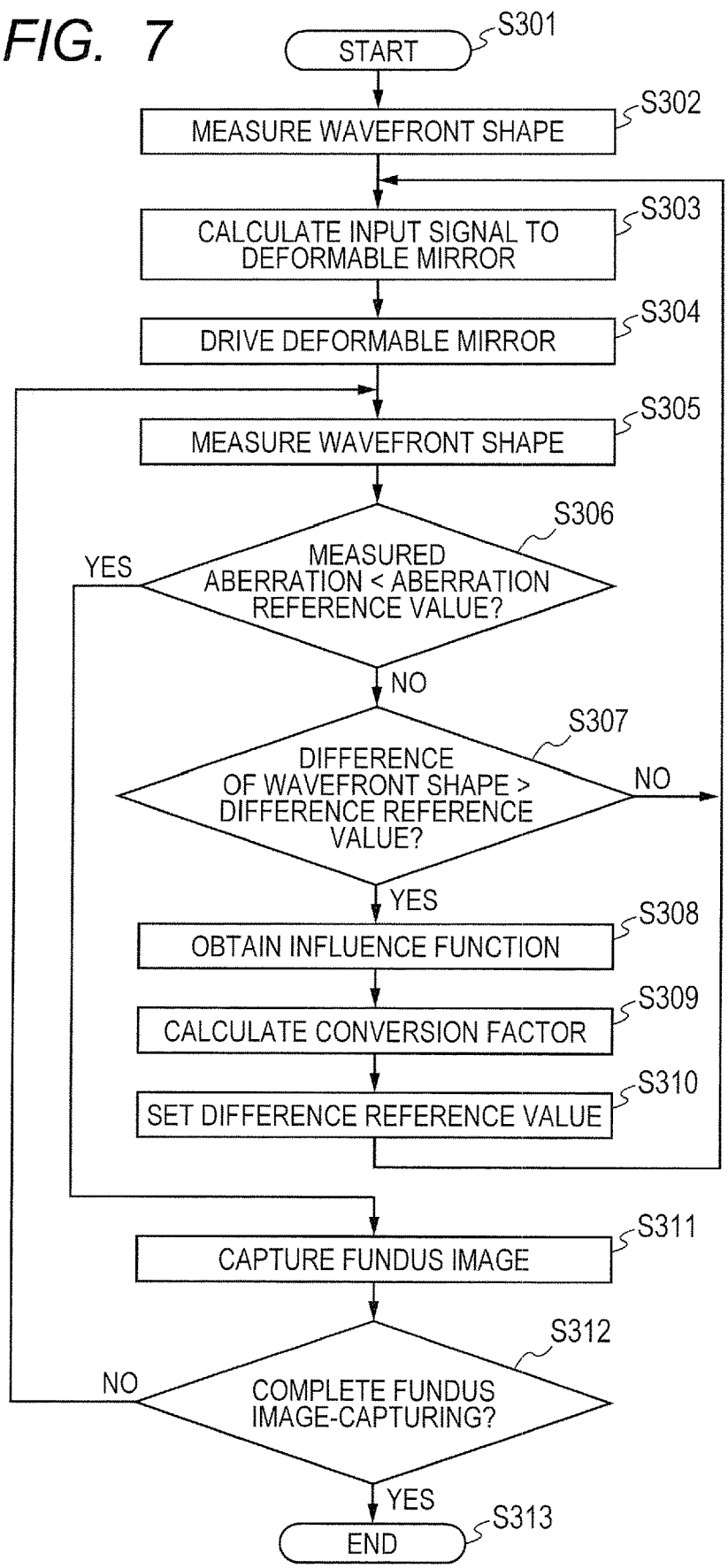
FIG. 7 is a flow chart of a process of capturing a fundus image in the first embodiment of the present invention.

FIG. 7 is a flow of using the AO unit to capture an image of the fundus while applying the above-mentioned invention to an ophthalmic apparatus.

In Step S301, the image capturing flow is started. In Step S302, a light wavefront shape of the reflected light or the like from the eye 111 is measured by the wavefront sensor 115. In Step S303, in accordance with the measured light wavefront shape, the input signal to the deformable mirror 108 required to correct the measured light wavefront shape is calculated. In Step S304, the deformable mirror 108 is driven in accordance with the given input signal. After the driving is finished, in Step S305, the light wavefront shape is measured again by the wavefront sensor 115. In Step S306, it is determined whether the measured aberration that has been measured again falls below the aberration reference value. In a case where it is determined here that the measured aberration falls below the aberration reference value, it is considered that the image of the fundus may be captured with the measured aberration, the flow advances to Step S311, and in Step S311, the image capturing of the fundus is executed. On the other hand, in a case where it is determined that the measured aberration does not fall below the aberration reference value, the flow advances to Step S307.

In Step S307, it is further determined whether the difference of the light wavefront shape exceeds the shape difference reference value described above. In a case where it is determined that the difference exceeds the shape difference reference value, the flow advances to Step S308, a process from Step S308 to Step S310 is performed, and the flow returns to Step S303. In other words, it is determined that the nonlinearity occurs in the relationship between the input signal and the deformation amount of the deformable mirror 108, and the obtainment of the influence function and the calculation of the conversion factor are executed again to set a new shape difference reference value. Then, in Step S303, the input signal is calculated in accordance with the new conversion factor obtained by the recalculation. The deformable mirror 108 is driven by the input signal, and Step S305 and the subsequent steps are executed again. Note that, at that time, when Step S307 is executed again, a newly set shape difference reference value is used.

In a case where it is determined in Step S307 that the difference does not exceed the shape difference reference value, it is determined that the problematic nonlinearity has not occurred at this point but that the measured aberration itself is large, and the flow returns to Step S303. In this case, the conversion factor is used without being changed in Step S303, and only the input signal is increased to increase the deformation amount of the deformable mirror 108. After the deformation amount is increased, the aberration is measured, and in Step S306, it is determined whether or not the aberration in the light wavefront shape is sufficiently corrected.

In a case where it is determined in Step S306 that the measured aberration falls below the reference value, after capturing the fundus image in Step S311, it is determined in Step S312 whether to end the image capturing. Here, in a case where the image capturing is to be continued, the flow returns to Step S305 to measure a new light wavefront shape in order to execute further image capturing. In a case where the image capturing is to be ended, the flow advances to Step S313, and the process is ended.

An effect obtained by executing the step of capturing the fundus image illustrated in the flow of FIG. 7 is described with reference to FIG. 8.

Figure 8:
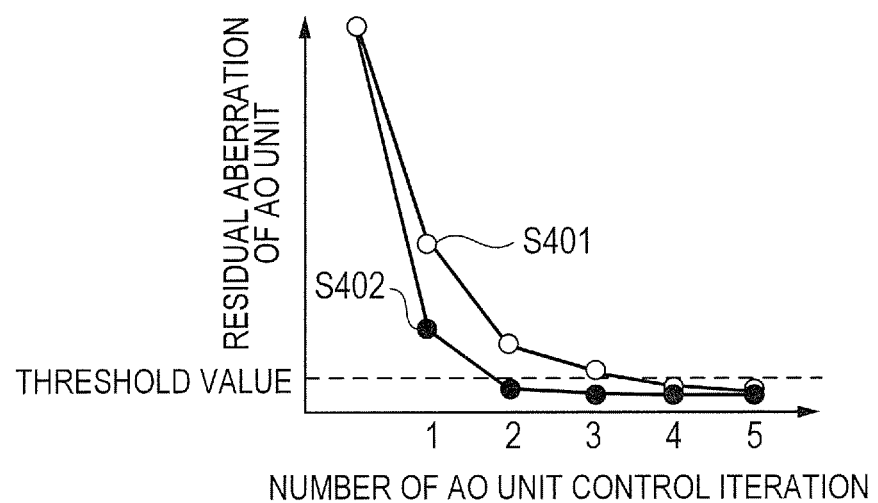
FIG. 8 is a graph for showing a relationship between the number of AO control iterations and residual aberration of AO processing.

In FIG. 8, a relationship of a change in amount of residual aberration in the reflected light or the like that has passed through the deformable mirror with respect to the number of control iterations executed by the AO unit is shown. Plots indicated by S401 indicate a case where a control by the related-art AO unit is performed, and plots indicated by S402 indicate a case where the control by the AO unit according to this embodiment is performed. An amount of residual aberration that does not cause a problem in capturing the image is also indicated as the threshold value by the dotted line.

In a case where the nonlinearity in the deformable mirror 108 has occurred, the deformation amount of the light wavefront shape with respect to the input value to the deformable mirror 108 is changed. Therefore, as indicated by S401, the aberration correction amount per AO control iteration does not become a desired amount, and the residual aberration remains. In the related-art case, the deformation amount of the deformable mirror 108 determined by the input signal is not actually obtained. Therefore, the measurement of the residual aberration and the setting and inputting of the input signal that is considered to correct the residual aberration in the case where linearity is obtained are repeated. When the conversion factor is updated while applying the present invention, the correction of the aberration per AO control iteration is performed more effectively as indicated by S402, with the result that the residual aberration converges to the threshold value or lower with a small number of AO control iterations.

As described above, according to this embodiment, the number of calculations is reduced while correcting the nonlinearity in the deformable mirror system utilized in the AO, and the time it takes to reach the desired light wavefront shape may be reduced.

Second Embodiment

<Fundus Imaging Apparatus>

A second embodiment of the present invention is described with reference to a flow chart of FIG. 9 by way of an example of a control method for a fundus imaging apparatus in a mode which is different from the first embodiment and to which the present invention is applied. In this embodiment, a basic apparatus configuration is similar to that in the first embodiment. Therefore, a description of the apparatus configuration is omitted, and a diopter correction process, which is characteristic in this embodiment, is described in detail.

Figure 9:
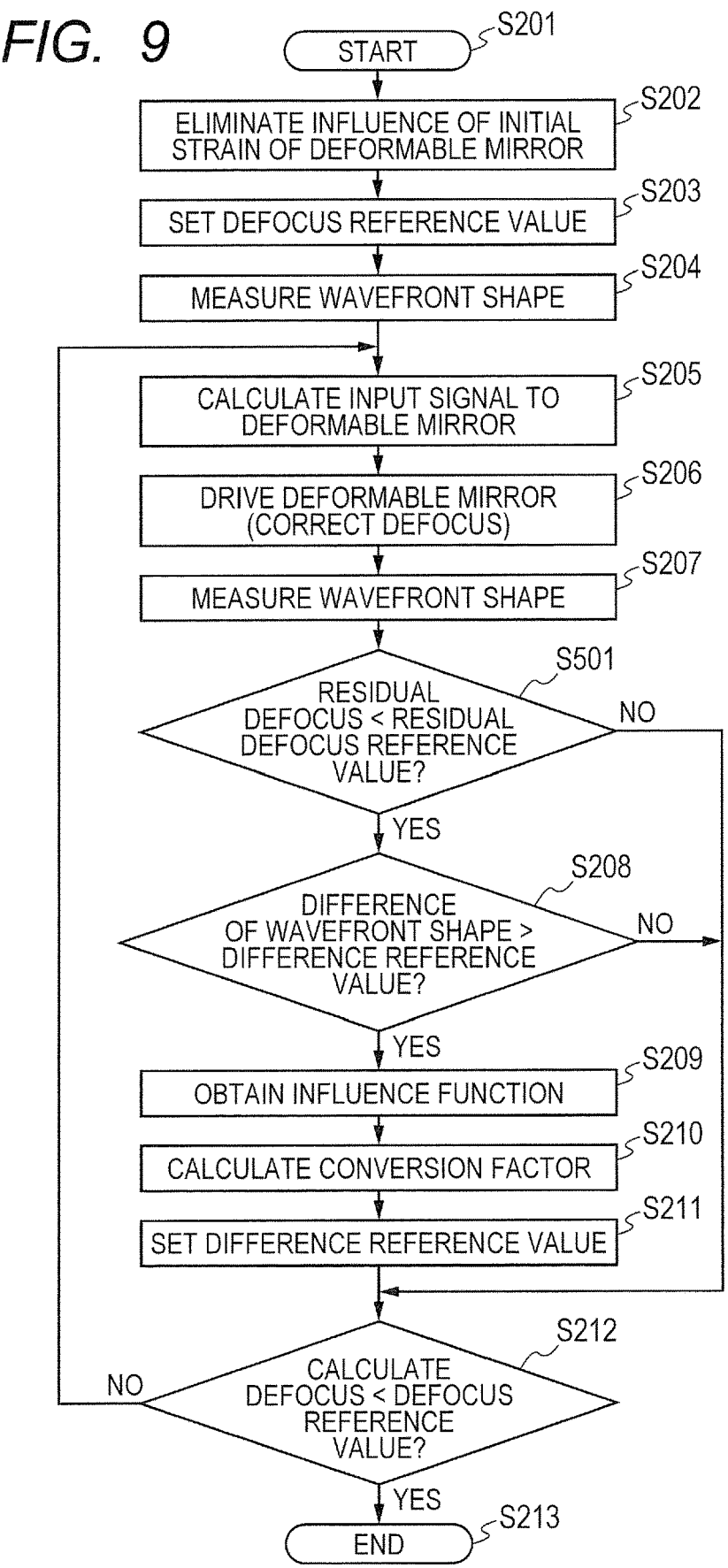
FIG. 9 is a flow chart of a diopter correction process in a second embodiment of the present invention.

FIG. 9 is a flow chart for performing the diopter correction process in this embodiment, and a basic flow is similar to that in FIG. 5. Therefore, a step that is different from the above-mentioned process is described here. After measuring the light wavefront shape of the reflected light or the like from the eye 111 in Step S207, the defocus amount is obtained based on the image obtained by the light intensity sensor 114 and the control unit 117, and in Step S501, it is determined whether the residual defocus amount falls below the residual defocus reference value. The term "residual defocus amount" as used herein refers to a defocus amount that still remains without being corrected after the defocus is corrected by the deformation of the deformable mirror.

In a case where it is determined in Step S501 that the residual defocus amount does not fall below the residual defocus reference value, the flow advances to Step S212, where the determination as to whether or not the defocus amount itself is larger than the defocus reference value is executed. Irrespective of the residual defocus amount, when the defocus amount itself is sufficiently small, it is determined that the image capturing is possible, and the flow proceeds to Step S213, where the process is ended. On the other hand, in a case where the residual defocus falls below the residual defocus reference value in Step S501, it is determined that the deformable mirror is in the vicinity of an operating point, and the flow advances to Step S208.

The term "operating point" as used herein refers to a state in which the deformable mirror is deformed into a target shape, and in this embodiment, to a state in which the deformable mirror is deformed so that the residual defocus becomes zero. As the residual defocus reference value, ±1 diopter is set, for example, and in a case where the deformable mirror falls within ±1 diopter of the operating point, a control may be made to transition to Step S208. An operation in Step S208 and the subsequent steps is similar to the operation in the embodiment illustrated in FIG. 5, and hence a description thereof is omitted here.

In other words, the control unit 117 described above updates, as the conversion factor update unit, the conversion factor within ±1 diopter, for example, which is a predetermined value range with respect to the operating point of the deformable mirror at which the reflected light from the deformable mirror 108 starts to have the light wavefront shape calculated based on the input signal.

An effect obtained by the flow of FIG. 9 is described with reference to FIG. 6C.

The residual defocus is an amount indicated by the bidirectional arrow in FIG. 6C. When the residual defocus falls below an amount indicated by a residual defocus reference value 3, the comparison between the difference of the light wavefront shape and the shape difference reference value in Step S208 is made. In the example shown in FIG. 6C, the difference of the light wavefront shape exceeds the shape difference reference value, and hence processing from Step S209 to Step S211 is performed. More specifically, the reobtainment of the influence function in Step S209, the recalculation of the conversion factor in Step S210, and the resetting of the shape difference reference value in accordance with the nonlinearity of the deformable mirror in Step S211 are performed.

According to this embodiment, the determination in accordance with the residual defocus amount may be added to further decrease the number of calculations during the diopter correction, and the effect of reducing the time it takes to capture the fundus image is obtained.

Third Embodiment

<Fundus Imaging Apparatus>

A third embodiment of the present invention is described with reference to a flow chart of FIG. 10 by way of an example of a control method for a fundus imaging apparatus in a mode which is different from the first embodiment and to which the present invention is applied. In this embodiment, a basic apparatus configuration is similar to that in the first embodiment. Therefore, a description of the apparatus configuration is omitted, and a diopter correction process, which is characteristic in this embodiment, is described in detail.

Figure 10:
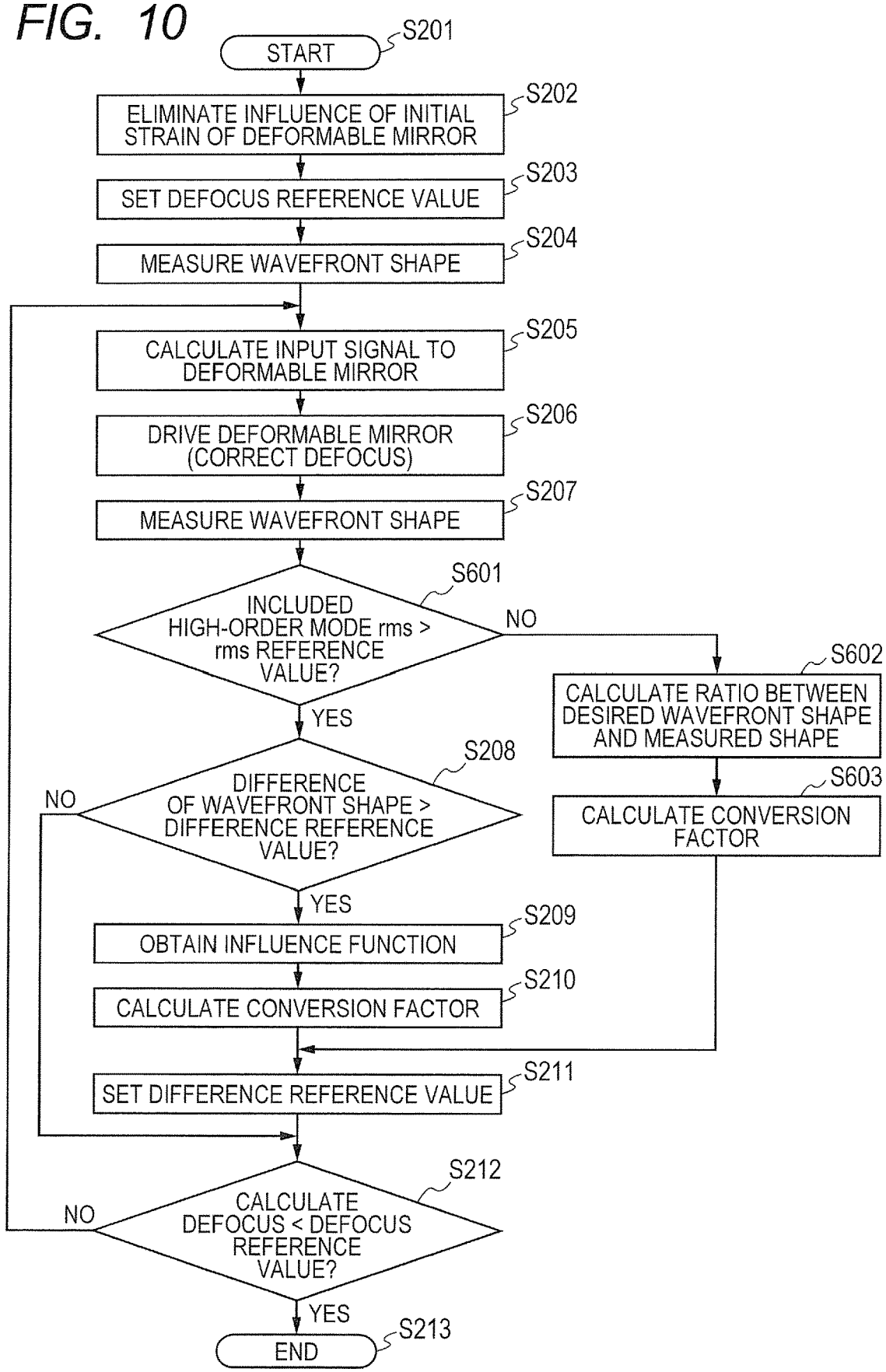
FIG. 10 is a flow chart of a diopter correction process in a third embodiment of the present invention.

FIG. 10 is a flow chart for performing the diopter correction process in this embodiment, and a basic flow is similar to that in FIG. 5. Therefore, a step that is different from the above-mentioned process is described here. After measuring the light wavefront shape of the reflected light or the like from the eye 111 in Step S207, it is determined in Step S601 whether a root mean square (rms) value of an included high-order mode obtained when the light wavefront shape is measured is larger than an rms reference value.

The term "included high-order mode" as used herein refers to a high-order mode of the light wavefront shape that intrinsically does not change but has been changed in correcting the defocus of the light wavefront shape by deforming the deformable mirror 108. This phenomenon occurs because, in a case where the deformation of the membrane is large, the drive amount with respect to the input signal to the individual actuators of the deformable mirror is changed.

In a case where it is determined in Step S601 that the rms value of the included high-order mode is larger than the rms reference value, the flow advances to Step S208. An operation in Step S208 and the subsequent steps is the same as in the case of the first embodiment, and hence a description thereof is omitted here. On the other hand, in a case where it is determined that the rms value of the included high-order mode is not larger than the rms reference value, the flow returns to Step S602. In the case where the included amount of the high-order mode is smaller than the rms reference value, it is considered that the situation may be addressed by adjusting only the deformation amount for the current deformation of the deformable mirror 108. Therefore, the conversion factor may be multiplied by a constant in constant multiplication to correct the conversion factor. In this case, the constant multiplication is executed by the conversion factor update unit.

More specifically, in Step S602, a ratio of a change in measured light wavefront shape to a change in desired light wavefront shape calculated based on the conversion factor and the input signal to the deformable mirror is calculated. Then, in Step S603, the conversion factor is multiplied by the ratio calculated in Step S602. Based on the conversion factor obtained by the proportional conversion, in Step S211 that follows, the shape difference reference value is set again, and the subsequent steps are executed.

According to this embodiment, the determination of the rms value of the included high-order mode and the reference value may be added to avoid the obtainment of the influence function and the calculation of the conversion factor, and the effect of reducing the time it takes to capture the fundus image is obtained.

According to the first to third embodiments described above, the number of calculations may be reduced while correcting the nonlinearity of the deformable mirror system utilized in the AO, and the time it takes to reach the desired light wavefront shape may be reduced. In other words, according to the embodiments described above, it is determined whether to calculate the conversion factor in accordance with the difference between the measured light wavefront shape and the desired light wavefront shape. Therefore, the conversion factor is not updated in the range of deformation amounts in which the linearity of the deformable mirror is maintained, and it is possible to obtain the effect that the time it takes to reach the desired light wavefront shape may be reduced. Moreover, in a range of variations in which the linearity is not maintained, the conversion factor is updated as appropriate. Therefore, as compared to the case where the feedback control is simply performed between the deformation amount and the value of the input signal, it is possible to obtain the effect that the deformable mirror may be deformed appropriately by the smaller number of correction operations.

Other Embodiments

Further, the present invention is not limited to the above-mentioned embodiments, and various modifications and alterations may be made thereto without departing from the spirit of the present invention. For example, in the embodiments described above, the case where the eye is the subject to be measured having the aberration is described, but the present invention may be applied to an object to be measured having optical aberration other than the eye. In this case, the present invention has an aspect as a deformable mirror system, for example, other than the ophthalmic apparatus. Therefore, it is desired that the present invention be regarded as an inspection apparatus exemplified by the ophthalmic apparatus, and that the eye to be inspected be regarded as an aspect of the object to be inspected.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-194829, filed Sep. 25, 2014, which is hereby incorporated by reference herein in its entirety.

What is claimed is:

1. A deformable mirror system comprising:
    a deformable mirror configured to change a shape of a reflecting surface by a deformation amount in accordance with an input signal;
    a light wavefront measurement unit configured to measure a light wavefront shape of reflected light via the deformable mirror; and
    a processor implementing steps comprising:
    (1) calculating the deformation amount to correct the light wavefront shape of the reflected light into a wavefront without an aberration;
    (2) calculating the input signal to input to the deformable mirror using a conversion factor based on the calculated deformation amount, the conversion factor being a correction value for a signal used in calculating the input signal to the deformable mirror required to change the light wavefront shape by a reference amount;
    (3) controlling the deformable mirror to change the shape of the reflecting surface in accordance with the calculated input signal;
    (4) calculating a variation amount of the light wavefront shape between a first light wavefront shape measured by the light wavefront measurement unit and a second light wavefront shape measured by the light wavefront measurement unit, wherein the first light wavefront shape is a light wavefront shape which was measured before the changing of the shape of the reflecting surface, and the second light wavefront shape is a light wavefront shape which was measured after the changing of the shape of the reflecting surface;
    (5) calculating a shape difference amount between the calculated variation amount and the calculated deformation amount; and
    (6) updating the conversion factor and implementing the steps (2) through (5) in a case of the calculated shape difference amount not satisfying a predetermined condition, and repeating the steps (1) through (5) in a case of the calculated shape difference amount satisfying the predetermined condition.

2. The deformable mirror system according to claim 1, wherein the updating updates the conversion factor based on a result of a comparison between the shape difference amount and a threshold value.

3. The deformable mirror system according to claim 2, wherein the processor further implements a step of changing the threshold value in accordance with the update of the conversion factor.

4. The deformable mirror system according to claim 1, wherein the updating updates the conversion factor in a predetermined value range with respect to an operating point of the deformable mirror at which the reflected light from the deformable mirror starts to have the light wavefront shape calculated based on the input signal.

5. The deformable mirror system according to claim 1, wherein the updating multiplies the conversion factor by a constant.

6. The deformable mirror system according to claim 1, wherein the processor further implements steps comprising:
   detecting a defocus amount with respect to an object to be inspected on which the reflected light is reflected; and
   permitting in accordance with a result of a comparison between the detected defocus amount and a defocus reference value, to capture an image of the object to be inspected using the reflected light.

7. The deformable mirror system according to claim 6, wherein the processor further implements steps comprising:
   calculating a residual defocus amount based on the detected defocus amount and the defocus amount calculated from the input signal; and
   comparing the calculated residual defocus amount and a residual defocus reference value to update the residual defocus reference value.

8. An ophthalmic apparatus comprising:
   a deformable mirror system according to claim 6,
   wherein the object to be inspected comprises an eye, and
   wherein the image comprises an image of a fundus of the eye.

9. A control method for a deformable mirror system, the control method comprising:
   (1) calculating a deformation amount to correct a first light wavefront shape of reflected light, the first light wavefront shape having been measured by a light wavefront measurement unit, into a wavefront without an aberration;
   (2) calculating an input signal to input to a deformable mirror using a conversion factor based on the calculated deformation amount, the conversion factor being a correction value for a signal used in calculating the input signal to the deformable mirror required to change the light wavefront shape by a reference amount;
   (3) controlling the deformable mirror to change a shape of a reflecting surface of the deformable mirror in accordance with the calculated input signal;
   (4) measuring a second light wavefront shape of reflected light via the changed reflecting surface of the deformable mirror;
   (5) calculating a variation amount of the light wavefront shape between the first light wavefront shape and the second light wavefront shape, wherein the first light wavefront shape is a light wavefront shape which was measured before the changing of the shape of the reflecting surface, and the second light wavefront shape is a light wavefront shape which was measured after the changing of the shape of the reflecting surface;
   (6) calculating a shape difference amount between the calculated variation amount and the calculated deformation amount; and
   (7) updating the conversion factor and implementing the steps (2) through (6) in a case of the calculated shape difference amount not satisfying a predetermined condition, and repeating (1) through (6) in a case of the calculated shape difference amount satisfying the predetermined condition.

10. A non-transitory recording medium having recorded thereon a program for causing a computer to execute each of steps of a control method for a deformable mirror system, the control method comprising:
   (1) calculating a deformation amount to correct a first light wavefront shape of reflected light, the first light wavefront shape having been measured by a light wavefront measurement unit, into a wavefront without an aberration;
   (2) calculating an input signal to input to a deformable mirror using a conversion factor based on the calculated deformation amount, the conversion factor being a correction value for a signal used in calculating the input signal to the deformable mirror required to change the light wavefront shape by a reference amount;
   (3) controlling the deformable mirror to change the shape of a reflecting surface of the deformable mirror in accordance with the calculated input signal;
   (4) measuring a second light wavefront shape of reflected light via the changed reflecting surface of the deformable mirror;
   (5) calculating a variation amount of the light wavefront shape between the first light wavefront shape and the second light wavefront shape, wherein the first light wavefront shape is a light wavefront shape which was measured before the changing of the shape of the reflecting surface, and the second light wavefront shape is a light wavefront shape which was measured after the changing of the shape of the reflecting surface;
   (6) calculating a shape difference amount between the calculated variation amount and the calculated deformation amount; and
   (7) updating the conversion factor and implementing the steps (2) through (6) in a case of the calculated shape difference amount not satisfying a predetermined condition, and repeating (1) through (6) in a case of the calculated shape difference amount satisfying the predetermined condition.

11. The deformable mirror system according to claim 1, wherein the processor further implements steps of:
   determining whether an aberration value of the second light wavefront shape falls below an aberration reference value; and
   capturing an image of an eye fundus in a case where it is determined that the aberration value falls below the aberration reference value.

12. The deformable mirror system according to claim 11, wherein the processor carries out the step of calculating the shape difference amount in a case where it is determined that the aberration value does not fall below the aberration reference value.

* * * * *